US008957376B1

(12) United States Patent
Tkachuk et al.

(10) Patent No.: US 8,957,376 B1
(45) Date of Patent: Feb. 17, 2015

(54) OPTOPAIRS WITH TEMPERATURE COMPENSABLE ELECTROLUMINESCENCE FOR USE IN OPTICAL GAS ABSORPTION ANALYZERS

(71) Applicant: Bah Holdings LLC, Glen Cove, NY (US)

(72) Inventors: Michael Tkachuk, South Setauket, NY (US); Sergey Suchalkin, Stony Brook, NY (US)

(73) Assignee: Bah Holdings, LLC, Glen Cove, NY (US)

( * ) Notice: Subject to any disclaimer, the term of this patent is extended or adjusted under 35 U.S.C. 154(b) by 0 days.

(21) Appl. No.: 14/268,360

(22) Filed: May 2, 2014

Related U.S. Application Data

(60) Provisional application No. 61/862,992, filed on Aug. 7, 2013.

(51) Int. Cl.
*G01J 5/20* (2006.01)
*G01N 21/3504* (2014.01)
*H01L 31/167* (2006.01)
*H01L 31/101* (2006.01)

(52) U.S. Cl.
CPC .......... *G01N 21/3504* (2013.01); *H01L 31/167* (2013.01); *H01L 31/101* (2013.01)
USPC ...................................... 250/338.4

(58) Field of Classification Search
USPC ...................................... 250/348.4
See application file for complete search history.

(56) References Cited

U.S. PATENT DOCUMENTS

| 4,286,327 | A  | * | 8/1981  | Rosenthal et al. ............... 702/23 |
| 5,670,777 | A  | * | 9/1997  | Inushima et al. .......... 250/214.1 |
| 6,144,681 | A  | * | 11/2000 | Capasso et al. .......... 372/45.013 |
| 2009/0268204 | A1 | * | 10/2009 | Tkachuk ....................... 356/437 |
| 2011/0284926 | A1 | * | 11/2011 | Chia ........................... 257/186 |

\* cited by examiner

*Primary Examiner* — David Porta
*Assistant Examiner* — Edwin Gunberg
(74) *Attorney, Agent, or Firm* — Intellectulaw; Panagiota Betty Tufariello, Esq

(57) ABSTRACT

Optopair for use in sensors and analyzers of gases such as methane, and a fabrication method therefor is disclosed. It comprises: a) an LED, either cascaded or not, having at least one radiation emitting area, whose spectral maximum is de-tuned from the maximum absorption spectrum line of the gas absorption spectral band; and b) a Photodetector, whose responsivity spectral maximum can be either de-tuned from, or alternatively completely correspond to the maximum absorption spectrum line of the absorption spectral band of the gas. Modeling the LED emission and Photodetector responsivity spectra and minimizing the temperature sensitivity of the optopair based on the technical requirements of the optopair signal registration circuitry, once the spectral characteristics of the LED and Photodetector materials and the temperature dependencies of said spectral characteristics are determined, provides the LED de-tuned emission and Photodetector responsivity target peaks respectively.

2 Claims, 12 Drawing Sheets

OPTOPAIRS WITH TEMPERATURE COMPENSABLE ELECTROLUMINESCENCE FOR USE IN OPTICAL GAS ABSORPTION ANALYZERS

CROSS-REFERENCE TO RELATED APPLICATIONS

This application claims priority from U.S. Provisional Application Ser. No. 61/862,992 filed on Aug. 7, 2013, which is incorporated by reference in its entirety as if more fully set forth herein.

BACKGROUND OF THE INVENTION

1. Field of Invention

This invention relates to an improved optical gas sensor with temperature compensable performance for the detection and determination of gas concentration by means of absorption spectroscopy, using non-dispersive radiation. More particularly, the present invention relates to an optopair for use in optical gas sensors and/or optical absorption gas analyzers, the optopair comprising an LED source and a corresponding Photodetector capable of reliable and consistent qualitative and quantitative analysis of gases at different temperatures, notwithstanding the optopair's sensitivity to temperature changes.

2. Prior Art

Absorption spectroscopy refers to spectroscopic techniques that measure the absorption of radiation, as a function of its frequency or wavelength, due to its interaction with a sample to be analyzed (analyte). The analyte absorbs some of the radiation, as it comes in contact with it. The amount of the radiation absorbed by the analyte varies as a function of the frequency of the radiation, and the concentration of the analyte (Beer-Lambert Absorption Law)[1], and this variation determines the absorption spectrum of the sample analyte. Thus, absorption spectroscopy is employed as an analytical tool to determine the presence of a particular analyte and, in many cases, to quantify the amount of the analyte present.

[1] Soinikova, G. Y., Low Voltage $CO_2$-Gas Sensor based on III-V Mir-IR Immersion Lens Diode Optopairs: Where are we and How Far we Can Go? *IEEE SENSORS JOURNAL*, 2009

Absorption spectroscopy, as an analytical tool, works by directing a generated beam of radiation at the analyte and detecting the intensity of the radiation that passes through it. The analysis of the transmitted radiation can be used to calculate the absorption and from the absorption the concentration of the analyte. The source, sample arrangement, and detection technique vary significantly depending on the frequency range and the purpose of the experiment.

Absorption spectroscopy methods utilize any type of radiation. Provided however, that the type of radiation utilized depends on the atomic structure and nature of chemical bonds of the analyte. Many gases are highly absorbent in the infrared spectral region. Absorption spectroscopy methods using infra-red radiation have long been recognized as sensitive, stable, and reliable methods for the detection and determination of the concentration of gases, in among other things, atmospheric air. If the measured parameter is the intensity of absorbed radiation at a fixed frequency or within a fixed frequency range, the spectroscopic method is called "non-dispersive." Such non-dispersive infra-red absorption measurement methods are based on the gases' molecular properties, which enable them to interact with and absorb infrared radiation within a certain spectral range.

When the gases are placed in the path of the infra-red radiation and the radiation's spectrum corresponds to the absorption spectrum of the gases, the gases will absorb such radiation.[2] Further, the gases will absorb the most when the wavelengths of maximum radiation intensity correspond to, coincide with, and match the wavelengths of maximum gas radiation absorption. More specifically, in a typical infra-red atomic spectroscopy method, the concentration of the gas of interest in a sample is determined once the absorption of the infra-red radiation by the gas has been detected and measured. As a result, non-dispersive infra-red absorption spectroscopy methods are widely used to detect many different gases, including carbon dioxide, carbon monoxide, methane, ethane, hydrogen sulfide and so on.

[2] Sotnikova, G. Y., Low Voltage $CO_2$-Gas Sensor Based on III-V Mid-IR Immersion Lens Diode Optopairs: Where are we and how far can We go? *IEEE Sensors Journal*, 2009.

Infra-red absorption spectroscopy instrumentation comes in more than one configuration. A typical "one channel" infra-red instrument ("sensor") comprises a source of radiation (usually infrared), such as an incandescent lamp or another electrically heated element that serves as a blackbody emitter, e.g., a silicon carbide rod or nichrome filament; a narrow bandpass filter arranged to ensure that only radiation intensity absorbed by the gas of interest is measured; a gas chamber for containing a sample including the target gas of interest; and a photodetector for detecting radiation transmitted by the sample and transforming the energy of the detected radiation into an electrical signal whose magnitude corresponds to the intensity of the detected radiation.

"Two channel" infra-red sensors have a signal channel and a reference channel. The signal channel operates in exactly the same way as the "one" channel device described above, with the transmission band of the band pass filter adjusted to the absorption wavelength(s) of the gas of interest. The reference channel usually works in another wavelength band, at which the target gas species does not absorb. This provides a base line for the signal channel. The differential signal between the signal and reference channels, normalized on reference channel intensity, gives an absorption signal which is stable with respect to any intensity drift resulting from the radiation source (or detector).

Another type of a "two channel" infra-red sensor comprises two photodetectors and includes two separate gas cells into which the emission from the radiation source is split along paths of equal lengths. One cell is filled with nonabsorptive (inert) gas to provide a reference channel, and the other with the sample gas (including the gas of interest). Both photodetectors work on the same wavelength (corresponding to an absorption wavelength of the target gas analyte) resulting in a sensor that is relatively stable and produces reliable results.

The instrument configurations described above present some serious design drawbacks when attempting to modify them for portable, in-situ field use, beyond the laboratory walls. For example, requiring a separate, sealed gas reference cell containing an inert gas results in an instrument configuration that is expensive, bulky, heavy and unwieldy. Similarly, using an incandescent bulb as the source of radiation in a portable instrument does not make sense because incandescent bulbs, which provide the necessary wide wavelength radiation band, result in a radiation source that is slow to respond (typically, the response time is more than 100 milliseconds) and requires significant power (200 milliwatts or more). As such, the instrument configurations described above are not suitable for portable, low power sensors which ideally should operate at a power consumption of no more than 1-2 milliwatts.

To resolve these drawbacks, portable infra-red sensors have been developed where semiconductors are used as both radiation sources and radiation detectors. The radiation sources are semiconductors that behave as light emitting diodes (LEDs). Likewise, the radiation detectors are semiconductors that behave as photodetectors (PDs). A number of such infra-red LED sensors are disclosed in the Tkachuk U.S. Letters Pat. No. 7,796,265 titled Optical Absorption Gas Analyzer, (the "265" patent), which is hereby incorporated by reference in its entirety as if more fully set forth herein.

The '265 patent discloses an analyzer comprising a chamber for containing the sample in use; a radiation source assembly arranged to emit radiation into the chamber; a first radiation detector assembly arranged to detect radiation transmitted along a first optical path through the chamber; a second radiation detector assembly arranged to detect radiation transmitted along a second optical path through the chamber, wherein the length of the second optical path which the sample can intercept is shorter than that of the first optical path; and a processor adapted to generate a sensing signal $S_S$ based on the detected radiation transmitted along the first optical path and a reference signal $S_R$ based on the detected radiation transmitted along the second optical path, and to determine the concentration of the target gas in the sample based on a comparison of the sensing signal with the reference signal.

By arranging for radiation to be detected along a second optical path which is shorter than the first, the '265 patent provides a reference channel which operates using the same radiation as the signal channel, yet does not require the provision of a separate (inert) cell, since both optical paths pass through the same chamber. The relatively short length of the second optical path with which the sample can interact (compared to that of the first optical path) means that absorption in the reference channel is suppressed and can be used to accurately compensate for drift. Preferably, the length of the second optical path with which the sample can interact is made as short as possible, and in any case significantly shorter than that of the first optical path. As a result any losses caused by absorption in the reference path will be small.

The '265 patent further discloses that LEDs or any other fast-response radiation source (a response time of less than or equal to 100 milliseconds, preferably less than 1 millisecond, still preferably less than 50 microseconds) can be used as the radiation source assembly arranged to emit radiation into the chamber, since both the signal and the reference channels can operate at the same or overlapping wavebands. Further, photodetectors and preferably photodiodes, can be used as the first and second detector assemblies.

Based on the foregoing, it appears that use of LEDs in portable infra-red instrument configurations may seem ideal. After all, LEDs are very fast; their response time is of the order of less than one micro-second. They provide greater selectivity of radiation. They have corrosive medium stability and longer periods of service and operation. And during all of that they consume very little power.[3]

[3] Sotinikova, G. Y. et. al., Performance analysis of diode optopair gas sensors, *Proc. Of SPIE*, 2009, Vol. 7356 735617; Sotnikova, G. Y. et. al., Low Voltage $CO_2$-Gas. Sensor Based on Mid-IR Immersion Lens Diode Optopairs: Where are we and how far can We go? *IEEE Sensors Journal*, 2009; Gibson D. et. al., A Novel Solid State Non-Dispersive Infrared $CO_2$ Gas Sensor Compatible with Wireless and Portable Deployment. *Sensors*, 2013, 13, 7079-7103.

By way of background, LEDs are semiconductor emitters. Semiconductor emitters and detectors appear to be the most prospective candidates for a optical absorbance gas analyzers and sensors due to reliable processing technology of semiconductors, high repeatability and precision of the semiconductor devices. The technology of molecular beam epitaxy (MBE) allows atomic level precision and makes possible production of multi-layer semiconductor structures while preserving the crystalline order throughout the entire structure.

One of the most important characteristics of the semiconductor material is the magnitude of its so-called "band gap". The band gap represents the energy range which is forbidden for the charge carriers inside the material. The band gap separates two allowed energy ranges: lower—"valence" band and higher—"conduction" band. In intrinsic semiconductors at low temperature the valence band is completely occupied by electrons while the conduction band is empty. To be excited to the conduction band, the electron has to obtain the minimum energy which is equal to the band gap energy or, simply, to the band gap. Excited electrons leave the vacancy in the valence band which behaves as a positively charged particle—"hole". When the excited electron returns back to the valence band (or, in other words, recombines with the hole), the minimum energy it can return is the bandgap energy. If the energy is returned in the form of electromagnetic emission, the wavelength of the emission is determined by the band gap. So the band gap determines the emission spectrum of the emitter and the responsivity spectrum of the detector.

In semiconductor alloys, the band gap magnitude can be controlled through the alloy composition. Molecular Beam Epitaxy (MBE) allows more precise way of the effective band gap control through the dimensional quantization effect. In a very thin layer of semiconductor materials (with the thickness of decades of the atomic layers and less) the charge carrier energy is determined both by the material bandgap and the thickness of the layer. If this layer is able to retain the carriers it is called "quantum well". The emitters based on quantum wells allow precise tuning of the band gap by variation of the quantum well width.

LEDs are some of the simplest semiconductor light emitters. Their composition and structure is such that when a current is applied to them, they emit light. As is shown in FIG. 1, a typical LED comprises two layers of semiconductor material. Each layer has a different type of conductivity, i.e., either n-type conductivity or p-type conductivity.

The conductivity type depends on the type of dopant introduced into the semiconductor material during its formation. Dopants are distinguished into "donors" and "acceptors." Introduction into the semiconductor material of dopants, which are "donors", produces an excess of mobile electrons, thereby resulting in a conductivity type which is negative: n-type. Introduction into the semiconductor material of dopants, which are "acceptors", leads to a majority of mobile holes, thereby resulting in a conductivity type which is positive: p-type.

As is shown in FIG. 2, in the region near the boundary between n- and p-type materials the electrons recombine with the holes and a depletion region is formed. The concentration of mobile carriers in the depletion region is reduced. The depletion region is also characterized by built-in electric field. When the external bias is zero, the diffusion currents of holes into the n-type layer and electrons into the p-type layer are compensated by the drift currents produced by the built-in electric field, so the net current is zero. When positive bias (plus to p-type, minus to n-type) is applied to the LED, as is shown in FIG. 3, the drift component of the current is suppressed and the net diffusion current appears in the structure.

Electrons and holes meet in the depletion region and recombine releasing energy in the form of photons. This effect is called electroluminescence The place where most of the electrons and holes recombine is called the emitter region or active region of the LED. The color of the light (corresponding to the energy of the photons released) and the wavelength of the LED radiation, is determined by the energy band gap (the energy difference in electron volts between the top of the valence band (n-type) and the bottom of the conduction band (p-type) of the LED.

Applications of semiconductor hetero-structures have led to breakthroughs in the technology of light emitters. A semiconductor hetero-structure is a layered semiconductor crystal. The layers have different band gaps but same lattice constant, so crystalline order is preserved throughout the entire stack of layers. Introduction of narrow band gap layers (quantum wells), which can accumulate injected electrons and holes provide for a high recombination efficiency and precise control of the emission wavelength. A typical band diagram of the quantum well (QW) LED is presented in FIG. 5.

Molecular Beam Epitaxy ("MBE") growth technology allows fabrication of quantum well LEDs, which can be used to create efficient cascaded LEDs. A cascaded LED structure includes several active regions connected in series. This injection scheme allows electron recycling so, one electron can produce more than one photon. Cascaded LEDs have increased power at a fixed current. Methods for the fabrication of cascaded LEDs are disclosed in the following articles, Jung, et. al., Light-Emitting Diodes Operating at 2 μm With 10 mW Optical Power, IEEE PHOTONICS TECHNOLOGY LETTERS, VOL. 25, NO. 23, Dec. 1, 2013; Prineas, et. al., Cascaded active regions in 2.4 μm GaInAsSb light-emitting diodes for improved current efficiency. *Applied Physics Letters* 2006, 89, 211108; Crowder, J G., et. al., Mid-infrared gas detection using optically immersed, room-temperature, semiconductor devices. *Meas. Sci. Technol.* 2002, 13, 882-884; Li, W. et. al., InGaAsSbN: A dilute nitride compound for midinfrared optoelectronic devices. *Journal of Applied Physics.* 2003, Vol. 94, No. 7, 4248-4250; Ashley, T. et. al., Uncooled InSb/In$_{1-x}$Al$_x$Sb mid-infrared emitter. *Applied Physics Letters* 1994, 64, 2433-2435; Shterenga, L. et. al., Type-I quantum well cascade diode lasers emitting near 3 m. *Applied Physics Letters* 2013, 103, 121108; Krier, A. et. al., The development of room temperature LEDs and lasers for the mid-infrared spectral range. *Phys. Stat. Sol.* (*a*), 2008, 205, No. 1, 129-143.

Likewise, by way of background, conventional photovoltaic detectors, i.e., photo-diodes ("PD") are fabricated in a manner that is similar to the fabrication of LEDs. In contrast to LEDs, however, PDs absorb photons and produce an electrical signal whose magnitude is determined by the intensity of the absorbed emission. So PDs operate in a manner that is the reverse of the operation of LEDs.

Conventional photo-diodes like LEDs comprise two layers of semiconductor material. Each layer has a different type of conductivity, i.e., either n-type conductivity or p-type conductivity. Like in LEDs, the conductivity type of each of the layers of the photo-diodes depends on the type of dopant introduced into the semiconductor material during its formation. Introduction into the semiconductor material of dopants, which are "donors", produces an excess of mobile electrons, thereby resulting in a conductivity type which is negative: n-type. Introduction into the semiconductor material of dopants, which are "acceptors", leads to a majority of mobile holes, thereby resulting in a conductivity type which is positive: p-type.

As a result, like in LEDs, the photo-diodes have a depletion region. Light in the form of photons absorbed in the depletion region of a photo-diode generates electrons and holes which are separated by the built in electric field. A schematic showing this operation principle of a photovoltaic detector is shown in FIG. 4. The motion of the generated electrons and holes in the depletion region creates a current whose signal can be measured precisely; but only when the signal to electron and hole generation noise ratio is high.

In accordance with Beer's-Lambert Absorption law (see discussion above), when the radiation produced by an LED passes through an analyte gas sample, the analyte gas sample will absorb energy as the radiation comes in contact with it. The amount of energy the analyte gas sample absorbs will vary as a function of frequency and wavelength of the radiation. The closer the frequency and wavelength of the radiation is to the corresponding frequency and wavelength of absorption line of the analyte gas sample, the larger the absorption of energy by the analyte gas sample. The larger the absorption the better and more reliable the signal to the photodiode detector, by which the detection and measurement the analyte gas sample is achieved.

Thus, in accordance with the foregoing, the following must be present for optimal optical gas sensor performance. First, the LED used as a radiation source and the photodetector used to read the absorption signal must be optically and spectrally matched (optopair). And, second, the energy and wavelengths of the radiation generated by the LED and directed on the analyte gas sample must coincide, correspond to and match the energy and wavelength of the maximum absorption line within the analyte gas sample's absorption spectrum.

However, due to the manner of LED production, it is very difficult to manufacture LEDs that consistently and reproducibly generate radiation whose energy and wavelengths coincide, correspond to and match the maximum absorption line within the gas' absorption spectrum. That is the reason why, many times optical gas sensors of the type described herein above are equipped with bandpass filters. The filters cut off all of the radiation emissions outside the target sample gas band, and enhance the relative magnitude of the absorbed emission. The filter is characterized by the spectral transmission function $F(\omega)=\Theta(\omega-\omega_1)-\Theta(\omega-\omega_2)$ where $\Theta$ is the step function.

But the use of LEDs and the photodetectors in portable infra-red instrument configurations, such as the optical gas sensors discussed above, is not without problems even if there are bandpass filters. First, the photodetectors discussed herein above produce noise during the generation of electrons and holes that could mask and interfere with the electric current generated thereby.

Second it is very well known that both the LEDs and the photodetectors are inherently sensitive to temperature changes. As the temperature changes, the LED emission spectrum broadens, its maximum spectral position shifts, and its intensity drops. Likewise, the amplitude and spectral position of the photo-detector responsivity drops and shifts respectively. Thus, these gas sensors cannot be reliable and suitable for the detection of gases in multiple environments having different temperatures. "The temperature shift of spectral characteristics of a source and detector of radiation inherent to all semiconductor elements and photoresistors without exception leads to changes of the optical sensor output signal and consequently, to errors in calculating the gas concentration."[4]

[4] Sotnikova, G. Y. et. al., Low. Voltage CO$_2$-Gas Sensor Based on III-V Mid-IR Immersion Lens Diode Optopairs: Where are we and how far can We go? *IEEE Sensors Journal,* 2009

More specifically, when an optical gas sensor equipped with an LED as its radiation source is taken out of an environment having one temperature and placed in an environment having a different temperature, the spectral position and intensity of the LED's radiation emission changes. As the temperature increases, the LED's band gap energy changes, resulting in a decrease of its luminescence intensity and a shift in its spectral position. And when it does shift, it will no longer correspond to the absorption line of the analyte gas sample, resulting in a much smaller absorption of radiation by the gas sample, a poor signal to the photodiode detector, and an unreliable detection and measurement of the gas.

In other words, when the temperature increases the spectrum maximum of the LED's emission radiation targeting the gas sample analyte will no longer coincide or correspond to the maximum of the absorption spectrum of the gas sample. As a result, the gas sample will absorb less of the radiation that comes in contact with it. The less the absorption of radiation by the gas sample, the less the photo-detector signal will be. The less the photo-detector signal, the more unreliable the detection and measurement of the gas sample will be.

Likewise, as the temperature increases, the peak of the photo-detector responsivity curve will shift to a lower wavelength side and its amplitude will decrease. As a result, the LED and the Photodetector will no longer be spectrally matched. This in turn will produce a signal that either does not register or is so small in value that it once again, it will be unreliable for the detection and measurement of the target sample gas.

Thus, as can be seen from the foregoing, an LED's power output and emitted radiation spectrum depend greatly on and will vary with the temperature of the environment the LED is being used in. Further, the LEDs' sensitivity to temperature changes is such an inherent characteristic of the LEDs' composition and structure, that many of the attempts to design around it up until now have used a totally different approach. See for example U.S. Letters Pat. No. 8,649,012 issued to Beckman et. al. and titled Optical Gas Sensor which attempts to solve the foregoing problem but in a manner that is totally different from the present invention. It discloses a sensor having a light-emitting diode, a photo-sensor, a measuring section between the light-emitting diode and the photo-sensor, and a control and analyzing unit, which is set up to determine the concentration of a gas in the measuring section from the light intensity measurement by the photo-sensor. The control and analyzing unit is set up to measure the forward diode voltage over the light-emitting diode at a constant current, to determine the temperature of the light-emitting diode from the detected forward diode voltage over the light-emitting diode by means of a preset temperature dependence of the forward diode voltage, and to apply a correction function as a function of the light-emitting diode temperature determined, with which the measurement is converted to that of a preset temperature of the light-emitting diode. See also U.S. Application Pub. No. US 2007/0035737 A1.

On the basis of the foregoing, it becomes evident that the LED radiation source in a portable infra-red gas sensor together with a photo-diode photodetector, chosen for optimal power output and emitted radiation wavelength at a certain temperature, will not have the same power output and emitted radiation at a different temperature. Thus, a single sensor will not be reliable and suitable for use in a wide environment temperature range. In other words, one who wants to use an infrared LED gas sensor in a room that is at 25° Celsius, would not be able to reliably use the same gas sensor in an environment that is at 60° Celsius. Use of a single infra-red LED gas sensor in multiple environments with different temperatures is unreliable.

A way to resolve the LED's reliability issue due to its sensitivity to temperature fluctuations, different from U.S. Letters Pat. No. 8,649,012 issued to Beckman (see discussion herein above) would be to use multiple sensors for measurements of gases at different temperatures. But that would result in having to keep multiple sensors at hand, one for each temperature at which a gas would have to be identified and quantified; something that would be extremely cumbersome, expensive and highly impractical.

Resolving the drawbacks in the prior art as discussed herein above is of paramount importance because among other things, reliable techniques for detecting methane and monitoring its concentration are in high demand in many industrial areas such as mining, construction, transportation of carbohydrate fuels and many others. The techniques need to be accurate enough to detect methane concentration below the methane lower explosive limit (LEL, 5% in atmosphere). A minimum accuracy of 1% is a must.

Methane has a low chemical activity. Accordingly, the chemical methods of methane detection are not effective and absorption spectroscopy through optical detection as described herein above, appears to be a promising path for methane sensing and analysis. However, any methane sensor implementing absorption spectroscopy must provide low power consumption and portability, with a 5-10 cm limit for the optical path of the probe emission. Further, it has to be able to feel changes of as low as 0.1% in the probe emission intensity. Finally it has to be based on detection of the change in the intensity of the probe emission in the absorption spectral range which is typical for methane only. Since no other atmospheric gases absorb in that range, any change of light intensity within the methane spectral range will indicate presence of methane and in accordance with Beers-Lambert Law of Absorbance, the magnitude of the absorption will be proportional to the concentration of methane gas sample analyte. Thus, the emission spectrum of the optopair light source should match to the optopair detector responsivity spectrum and the methane absorption band.

One of the strongest and most prominent vibration-rotation absorption bands of methane is near wavelength $\lambda=3.3$ μm ($\sim 3000$ cm$^{-1}$), which is within the mid-IR spectral range. So the emitter and detector should have their spectral characteristics peaked near 3.3 μm.

The bandgap of the emitter and detector material for methane sensing has to be around 0.367 eV which corresponds to $\lambda=3.3$ μm. This band gap belongs to relatively narrow band materials and it means strong temperature dependence of the materials' properties in the temperature range 240-330K. (−40 C to +60 C). This is a serious obstacle for developing a semiconductor based optopair which can reliably operate in this temperature range, which is essential for outdoor standalone methane sensors. Upon information and belief, no semiconductor methane sensors operating in this temperature range exist.

SUMMARY OF THE INVENTION

Accordingly there still exists a need for an optical gas sensor which is portable, light to carry, relatively inexpensive to manufacture and produce, capable of consuming very little power and equipped to deliver accurate and reliable qualitative and quantitative analysis of gases at multiple temperatures and at low concentrations. More particularly, there still exists a need for an optical gas sensor capable of identifying and measuring the absorbance of methane at below the lower explosive limit (LEL) of methane, i.e., 5% by volume in atmosphere, based on methane's absorption of infra-red radiation, across a broad range of environment temperature. There still exists a need for an optopair for use in a gas sensor that accurately and precisely detects and measures the concentration of a gas, irrespective of temperature, as a result of the optopair's structure and the compensable temperature susceptibility of the optopair signal resulting therefrom.

It is therefore an object of the present invention to provide an apparatus, process for production thereof and absorption spectroscopy technique which can produce a temperature compensable optopair signal, and which as a result can reliably and effectively detect and measure the absorbance of gas in environments across a broad range of temperatures, at low concentrations.

It is a further object of the present invention to provide an apparatus, process for production thereof and absorption spectroscopy technique for reliably and effectively detecting and measuring gases in environments across a broad range of temperatures and at low concentrations, said apparatus having a low power consumption and being highly portable.

It is still another object of the present invention to provide an apparatus, process for the production thereof and absorption spectroscopy technique for reliably and effectively detecting and measuring methane gas in environments across a broad range of temperatures, said apparatus being so sensitive that it is able to detect changes in the emission energy transmitted through the methane, of as little as 0.1%.

In accordance with the present invention there is provided an optopair for use in optical sensors for the analysis of an atmospheric gas sample ("target gas analyte"); namely the detection and determination of the concentration of the target gas analyte in atmosphere irrespective of temperature. The optopair comprises one radiation source and one radiation detector. The radiation source is an LED which has at least one active area capable of emitting radiation whose spectral maximum is de-tuned from, i.e., does not correspond or coincide with the maximum absorption spectrum line of the absorption spectral band of the target gas analyte. The active area of the LED can be a bulk, quantum-well or super-lattice active area.

Alternatively, the LED can be cascaded, with two or more cascades, each cascade having an active area, which can be a bulk, quantum-well, or super-lattice active area. Or the cascaded LED can have two or more cascades, each respectively having a bulk, quantum well or super-lattice active area, one of which has a spectral maximum that is de-tuned from the maximum absorption spectrum line of the absorption spectral band of the target gas analyte.

The radiation detector in turn is a photodetector ("PD") whose responsivity spectral maximum can be either de-tuned from the maximum absorption spectrum line of the absorption spectral band of the target gas analyte, or completely correspond to and coincide with the maximum absorption spectrum line of the absorption spectral band of the target gas analyte. It can comprise a sequence of a contact layer, a middle barrier layer and an n-type photon absorbing layer arranged such that the top energy of the valence band of the contact layer is not more than the bottom energy of the conduction band of the n-type photon absorbing layer, and the middle bather layer has an energy band gap significantly greater than that of the photon absorbing layer. Optionally, its contact layer can be a p-type contact layer.

The process of designing and fabricating an optopair suitable for use in a gas sensor, for the detection and accurate and precise measurement of a target gas analyte in a specific temperature range, as for example in a temperature range from −40° C. to 60° C., includes: the identification of the wavelengths that define the shortest, longest, and maximum spectral peak wavelengths of the absorption band of the target gas analyte; the use of the wavelengths to determine the material systems for the LED and the PD; the determination of the spectral characteristics of the LED and PD materials and the temperature dependencies of said spectral characteristics; the selection of the LED emission spectrum target peak wavelength, de-tuned from the maximum spectral absorption peak wavelength of the target sample gas analyte and the selection of the PD responsivity spectrum target peak wavelength, either de-tuned from, or in tune with, the maximum spectral absorpotion peak wavelength of the target sample gas analyte respectively, through modeling of the LED emission and the Photodetector responsivity spectra using the information generated by the preceding steps and minimizing the temperature sensitivity of the optopair as determined by the technical requirements of the signal registration circuitry of the optopair; and if necessary, further minimizing the temperature sensitivity of the optopair as dictated by the technical requirements of the signal registration circuitry of the optopair by alternatively identifying the target peak wavelengths for a multi-cascade LED emission spectrum for use in the optopair.

These and other objects, advantages, features and characteristics of the invention will be apparent from the following description of a preferred embodiment, considered along with the accompanying drawings.

BRIEF DESCRIPTION OF THE DRAWINGS

It is believed that the present invention will be better understood from the following detailed description taken in conjunction with the accompanying drawings, in which the numerals represent identical elements and wherein.

DETAILED DESCRIPTION OF THE INVENTION

Figure 1:
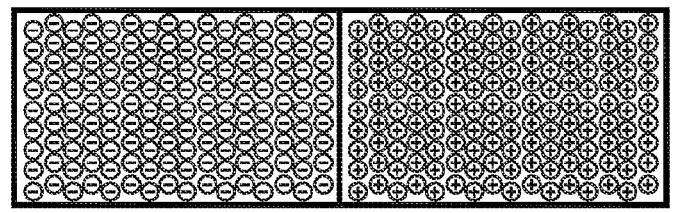
FIG. 1 is a simple schematic of a typical semiconductor diode (PRIOR ART)
Figure 2:
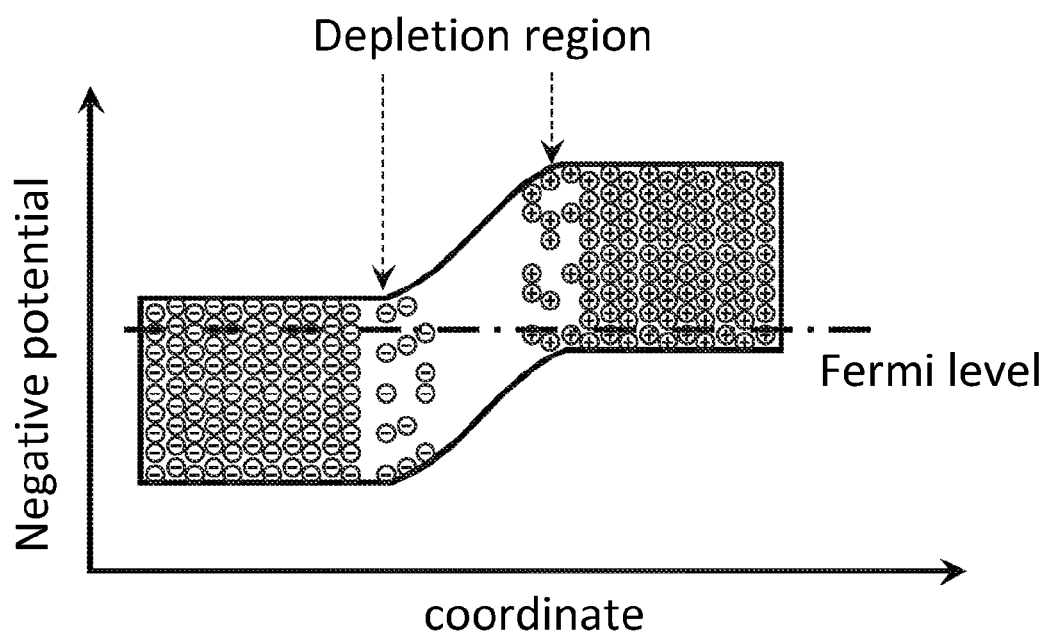
FIG. 2 is a schematic band diagram of a homo-diode (PRIOR ART)
Figure 3:
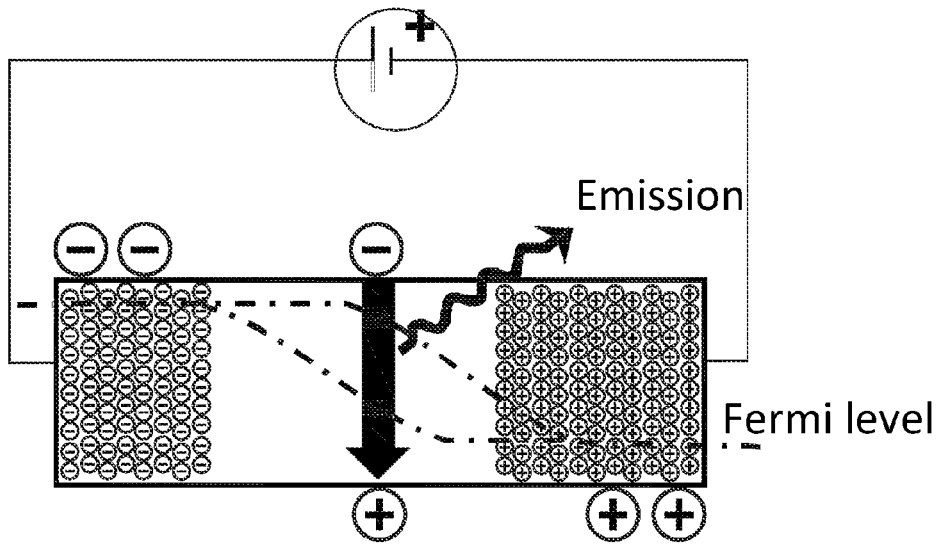
FIG. 3 is a schematic showing the operation of an LED under direct bias (PRIOR ART)
Figure 4:
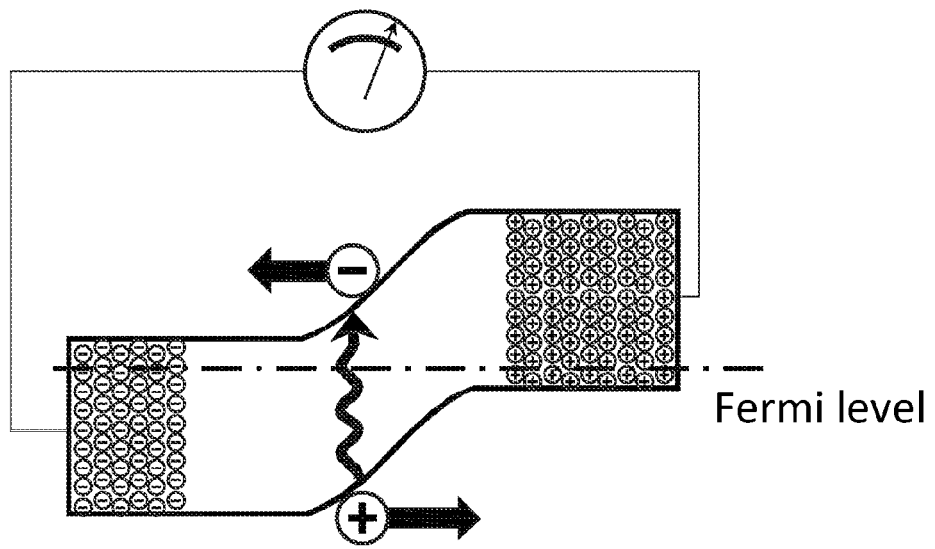
FIG. 4 is a schematic showing the operation principle of a photovoltaic detector (PRIOR ART)

The optopair of the present invention can be used with any number of optical gas sensors, schematic views and detailed descriptions of some of which are disclosed in the following patents and patent applications, the disclosures of which are incorporated and made a part of the present description by reference, as if more fully set forth herein: Tkachuk, Optical Absorption Gas Analyzer, U.S. Letters Pat. Nos. 7,796,265 B2 and 8,665,424 B2; Tkachuk, Optical Gas and/or particulate sensors, U.S. Letters Patent No. 8,692,997 B2; Tkachuk, Gas Sensor, U.S. patent application Ser. No. 13/426,494; Tkachuk, and Optical Absorption spectrometer and method for measuring concentration of a Substance, U.S. Letters Pat. Nos. 7,570,360 B1.

The optopair of the present invention comprises at least one radiation source and one radiation detector, which as is described in more detail herein below, are relatively optically and spectrally matched.

The radiation source of the optopair of the present invention is an LED, engineered to emit radiation having at least one wavelength/frequency, which is "de-tuned" from the peak absorption wavelength/frequency of the target sample gas analyte. In other words, the spectral maximum of the radiation generated by the LED of the optopair is "de-tuned" from the maximum absorption spectrum line of the absorption spectral band of the target gas being analyzed. Alternatively, the LED of the optopair of the present invention can be engineered to emit two or more radiations, each optionally having a slightly different wavelength or frequency from the other, and at least one of such two or more radiations being "de-tuned" from the peak absorption wavelength or frequency of the target sample gas.

As has been discussed above, optical methods of detection and quantification of gases, as for example Non-Dispersive Infra-Red (NDIR) methods, rely on the fact that many gases absorb at a very specific wavelength of infra-red radiation.[5] Thus, conventional wisdom in the absorption spectroscopy field dictates that the wavelength of the infra-red radiation generated by a radiation source and used to detect and measure an analyted target gas sample must match the peak absorption wavelength of the infra-red radiation capable of being absorbed by the analyte target sample gas. Or, the frequency of the radiation used to detect and measure the target gas analyte, must match the frequency of the infra-red radiation that the target gas analyte can absorb. In other words, the wavelength or frequency of the radiation generated by a radiation source and used to detect and measure the target analyte gas sample must match or be "tuned to", or be "in tune" with the wavelength or frequency of the radiation that the target analyte gas can absorb. For example, if the target analyte gas sought to be detected and measured is $CO_2$, then the wavelength of the radiation directed on the target analyte gas sample must be tuned to 4.26µ; the wavelength of radiation capable of being absorbed by $CO_2$.[6] If the target analyte gas sample sought to be detected and measured is methane ($CH_4$), then the wavelength of the radiation must be tuned to 3.3µ; the wavelength of radiation capable of being absorbed by $CH_4$.

[5] Gibson, D; MacGregor C. A Novel Solid State Non-Dispersive Infrared $CO_2$ Gas Sensor Compatible with Wireless and Portable Deployment. *Sensors* 2013, 13, 7079-7103.

[6] Id.

The design of the optopair of the present invention defies the foregoing conventional wisdom. The LED of the optopair of the present invention is engineered to emit at least one narrow wave band of radiation in the infra-red spectrum, the wavelength of which does not match, does not coincide with, does not correspond to and is NOT tuned to the wavelength or frequency of the radiation capable of being absorbed by the target sample gas analyte. It is "de-tuned." And it is de-tuned such that the emitted radiation's spectral maximum wavelength or frequency can be de-tuned either to the short wavelength/frequency of the maximum absorbance wavelength that corresponds to the maximum absorption spectrum line of the absorption spectral band of the analyte target gas; or to the long wavelength/frequency. For example, if the optopair is to be used for the detection of methane, and the LED is engineered to emit only one narrow wave band of radiation in the infra-red spectrum, then the wavelength of the radiation generated by the LED will not be 3.3µ. Rather it may be anywhere from 3.14 to 3.25.

If the LED radiation source is engineered to emit at least two narrow wave bands of radiation in the infra-red spectrum, then the spectral maximum of either of or both narrow wave bands' radiation is de-tuned from the wavelength or frequency corresponding to the maximum absorption spectral line of the absorption spectral band of the analyte target gas. For example, if the LED radiation source is engineered to emit at least two narrow wave bands of radiation to be used for the detection and quantification of methane, then the wavelength of the two narrow wavebands of emitted radiations may be around 3.18 and 3.3 microns (µ) respectively; or 3.18 and 3.4 microns (µ) respectively.

Preferably, in one embodiment of the inventive optopair, where the LED radiation source is engineered to emit only one narrow wave band of radiation in the IR spectrum whose wavelength is de-tuned from the maximum absorbance wavelength of, for example methane, i.e., 3.3µ, such radiation source may comprise a single Quantum Well LED, having only one emitter region ("active area") capable of generating radiation at a single wavelength.

Figure 5:
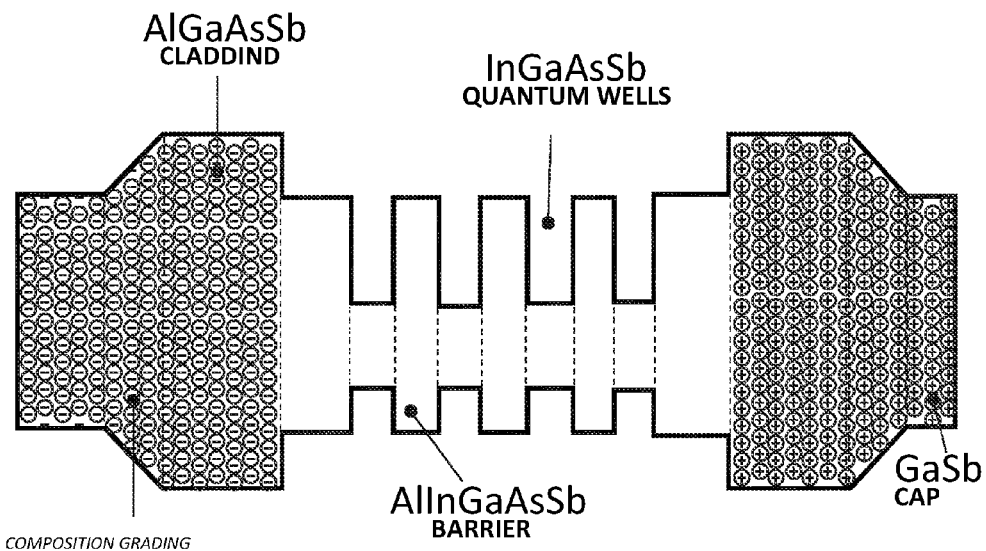
FIG. 5 is a band diagram of a GaSb-based QW LEDs (PRIOR ART)

Such LED is designed and made by forming a layered semiconductor crystal. The layers of the semiconductor crystals have different band gaps but same lattice constant, such that crystalline order is preserved throughout the entire stack of layers. The band gaps are narrow (quantum wells) which can accumulate injected electrons and holes, thereby allowing high recombination efficiency and precise control of the emission wavelength sufficient to de-tune the wavelength of the radiation that the band gaps create from the wavelength of maximum absorbance of the target gas. A typical band diagram of the quantum well LED used as the radiation source in the optopair of the present invention is presented in FIG. 5

(Prior Art). If the LED emitter region comprises no quantum wells, then the wavelength of the narrow band gap radiation it generates, cannot be de-tuned from the maximum absorbance wavelength of the target gas.

The general process of growing Quantum Well LEDs used in the optopair of the present invention is described in detail in Suchalkin, S. et. al., GaSb based Light Emitting Diodes with Strained InGaAsSb Type I Quantum Well Active Regions. *Applied Physics Letters* 2008, 93, 081107, the disclosure of which is incorporated by reference in its totality as if more fully set forth herein. Table I herein below discloses at least 5 different Quantum Well LED structures which have been grown in accordance with the process described in Suchalkin. S. et. al., GaSb based Light Emitting Diodes with Strained InGaAsSb Type I Quantum Well Active Regions. *Applied Physics Letters* 2008, 93, 081107. Two of such Quantum Well LEDs have been refined precisely to produce radiation whose wavelength is de-tuned from, i.e., tuned to the short wavelength of the maximum absorbance wavelength of methane. Incidentally, the Quantum Well LED structure identified as Device 5, in Table I, is a Quantum Well LED structure with one emitter region that produces radiation that is tuned exactly to the maximum absorbance wavelength of methane, i.e., 0.374 eV equivalent to 3.3μ.

ing to the maximum absorption spectrum line of the absorption spectral band of the target gas sample.

For example, when the optical gas sensor incorporating the present inventive optopair was designed to be used for the analysis of methane in temperatures that range from −40 degrees Celsius to 50 degrees Celcius, then the first emitter region of the cascaded LED emitted energy having a frequency at 0.36 eV (3.44μ); and the second emitter region of the cascaded LED emitted energy at a frequency of 0.39 eV (3.18μ). When the optical gas sensor incorporating the present inventive optopair was designed to be used for the analysis of methane in temperatures that range from minus40 degrees C. to 60 degrees C., the cascaded LED was provided with three emitter regions arranged in series. The first emitter region emitted energy having a frequency at 0.36 eV (3.44μ). The second emitter region emitted energy at a frequency of 0.39 eV (3.18μ). And the third active area emitted energy at 0.40 eV (3.09μ).

Processes for growing cascaded LEDs for use in the optopair of the present invention are described in detail in the following: Prineas, et. al., Cascaded active regions in 2.4 μm GaInAsSb light-emitting diodes for improved current efficiency. *Applied Physics Letters* 2006, 89, 211108. Crowder, J G., et. al., Mid-infrared gas detection using optically

TABLE I

The parameters of the device structures.

| Device | Cladding | Barrier | QW | Number of QWs | QW width, nm |
|---|---|---|---|---|---|
| 1 | $Al_{0.9}GaAs_{0.07}Sb$ | $Al_{0.35}GaAs_{0.03}Sb$ | $In_{0.55}GaAs_{0.22}Sb$ | 10 | 12 |
| 2 | $Al_{0.6}GaAs_{0.05}Sb$ | $Al_{0.2}In_{0.25}GaAs_{0.24}Sb$ | $In_{0.54}GaAs_{0.24}Sb$ | 4 | 17 |
| 3 | $Al_{0.6}GaAs_{0.05}Sb$ | $Al_{0.2}In_{0.2}GaAs_{0.2}Sb$ | $In_{0.54}GaAs_{0.24}Sb$ | 4 | 17 |
| 4 | $Al_{0.9}GaAs_{0.07}Sb$ | $Al_{0.35}GaAs_{0.03}Sb$ | $In_{0.55}GaAs_{0.22}Sb$ | 5 | 12 |
| 5 | $Al_{0.85}GaAs_{0.07}Sb$ | $Al_{0.2}In_{0.25}GaAs_{0.24}Sb$ | $In_{0.56}GaAs_{0.21}Sb$ | 3 | 14 |

Figure 20:
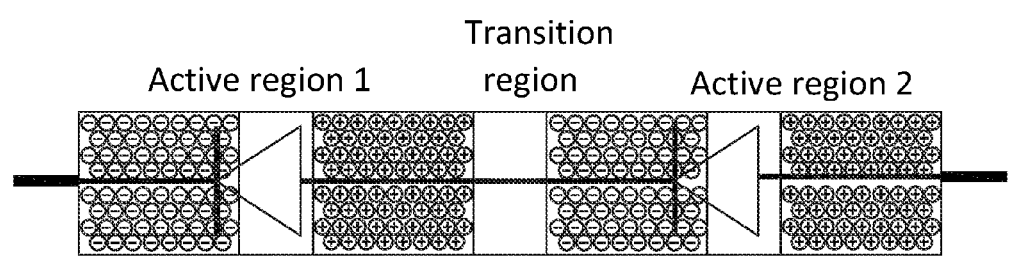
FIG. 20 is a schematic layout of a two cascade LED.
Figure 21:
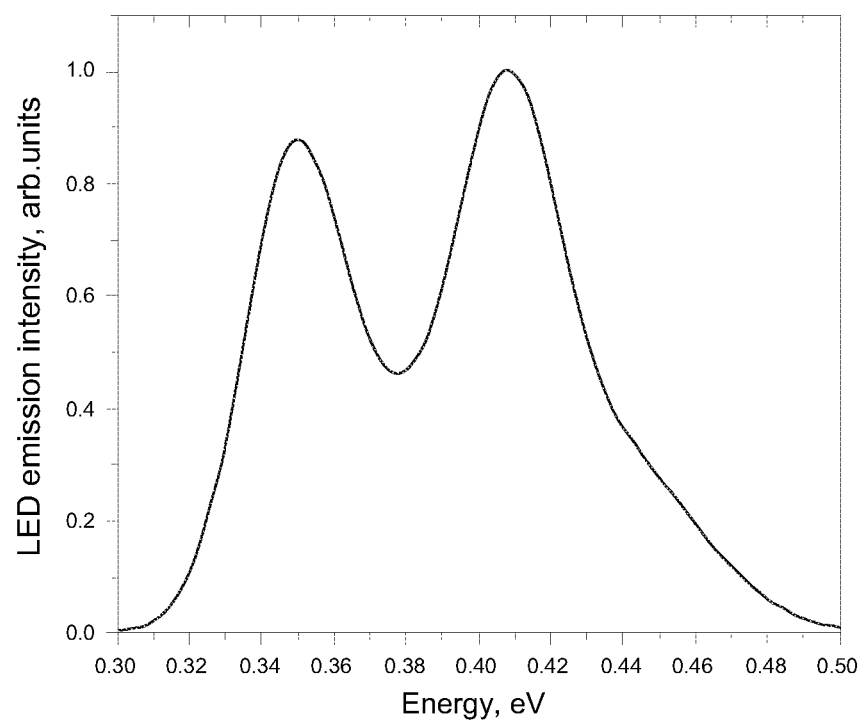
FIG. 21 is a schematic showing a simulated spectrum of two-cascade LED.

In another embodiment of the inventive optopair, where the LED radiation source is engineered to emit at least two narrow wave bands of radiation in the IR spectrum, whose wavelengths are de-tuned from the maximum absorbance wavelength of methane, i.e., 3.3μ, such LED radiation source comprises a cascaded LED, having at least two emitter regions ("active areas") in series, each one capable of generating radiation at a single wavelength (see FIG. 20). The wavelengths of the radiation of the two active areas in series of the cascaded LED can exactly match, or be exactly tuned to, the wavelength corresponding to the maximum absorption spectrum line of the absorption spectral band of the target gas sample. Or the wavelength of the radiation of one active area of the cascaded LED can exactly match, or be exactly tuned to, the wavelength corresponding to the maximum absorption spectrum line of the absorption spectral band of the target gas sample, and the radiation of the other active area of the cascaded LED can be de-tuned to either the short side or the long side of the wavelength corresponding to the maximum absorption spectrum line of the absorption spectral band of the target gas sample. Or the wavelengths of the radiation of both active areas are both de-tuned to different wavelengths on the short side of the wavelength corresponding to the maximum absorption spectrum line of the absorption spectral band of the target gas sample. Or, the wavelength of the radiation of one active area is de-tuned to the short side of the wavelength corresponding to the maximum absorption spectrum line of the absorption spectral band of the target gas sample and the wavelength of radiation of the other active area is de-tune to the long side of the wavelength correspond-immersed, room-temperature, semiconductor devices. *Meas. Sci. Technol.* 2002, 13, 882-884. Li, W. et. al., InGaAsSbN: A dilute nitride compound for midinfrared optoelectronic devices. *Journal of Applied Physics.* 2003, Vol. 94, No. 7, 4248-4250. Ashley, T. et. al., Uncooled InSb/$In_{1-x}Al_xSb$ mid-infrared emitter. *Applied Physics Letters* 1994, 64, 2433-2435. Shterenga, L. et. al., Type-I quantum well cascade diode lasers emitting near 3 m. *Applied Physics Letters* 2013, 103, 121108. Krier, A. et. al., The development of room temperature LEDs and lasers for the mid-infrared spectral range. *Phys. Stat. Sol.* (a), 2008, 205, No. 1, 129-143, the disclosures of which are incorporated in the present detailed description by reference in their totality as if more fully set forth herein.

Using the processes set forth herein above one embodiment of the cascaded LEDs was grown on GaSb substrates using a Veeco GEN930 MBE system. The emitting area of the cascaded LED comprised 2 cascaded emitter regions connected with a transition region. Each cascade included four compressively (~4.47%) strained In0.55Ga0.45As0.3Sb quantum wells separated by 50 nm Al0.2In0.55Ga0.25As0.23Sb bathers and doped GaSb claddings. The emission wavelength was controlled by adjusting the In content in the Quantum Well material and the quantum well width. The active region of the first cascade was sandwiched between doped GaSb claddings. The n-cladding of the second cascade was GaSb while the p-cladding was compositionally graded from Al0.5Ga0.5As0.43Sb to GaSb. To prevent hole leakage, the 12 A AlSb/12 A InAs superlattice hole blockers were inserted between n-cladding and bather in each cascade. The GaSb substrate was n-doped with Te to 2~3×1017 cm−3, the 500 A n-GaSb buffer layer grown on the substrate was doped to 5×1017 cm−3. A 10 nm thick Be doped (1×1019 cm−3) p+GaSb cap was grown on top of the structure.

Figure 6:
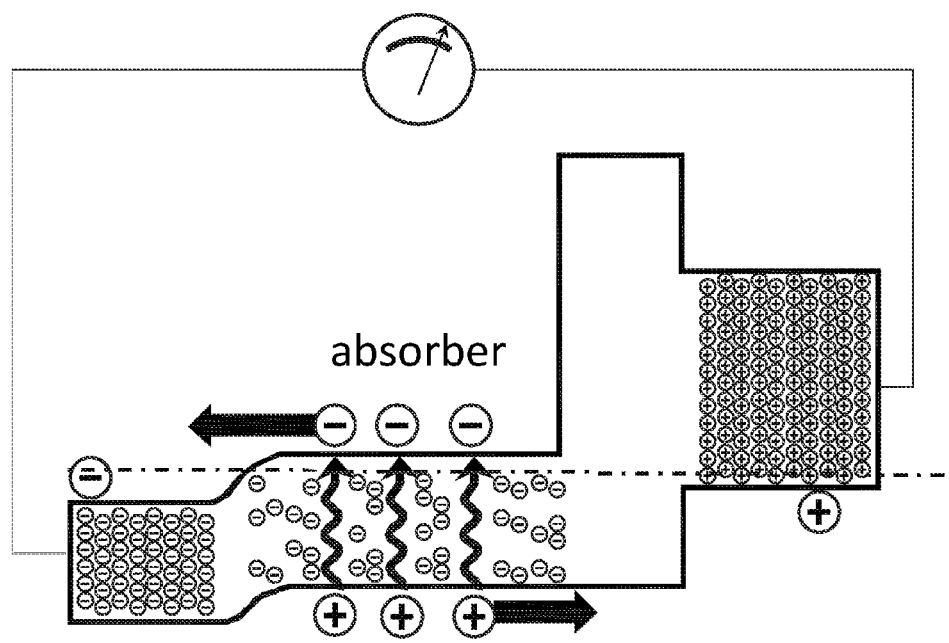
FIG. 6 is a schematic showing the operation principle of the inventive nBp Photodetector used in the inventive optopair.
Figure 17:
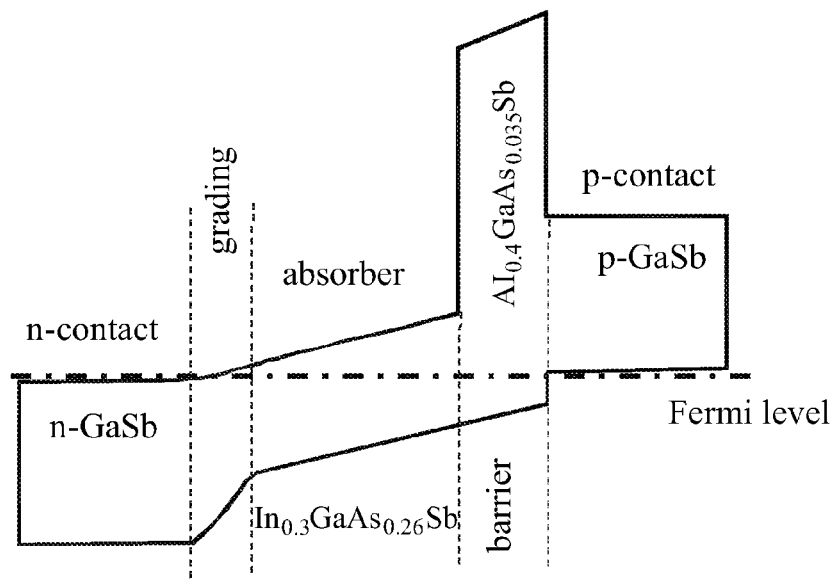
FIG. 17 is a band diagram of the inventive optopair photodetector.
Figure 18:
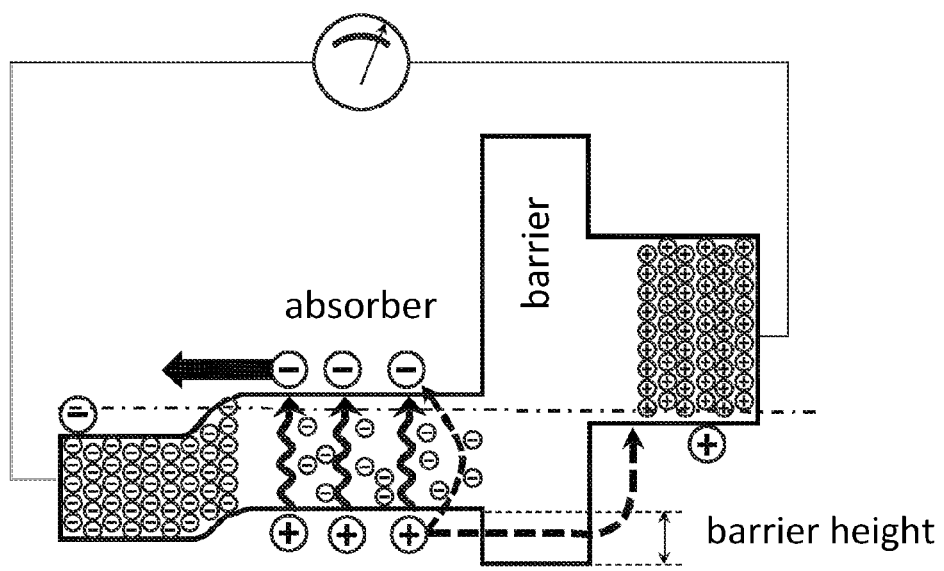
FIG. 18 is a schematic of an nBp photo detector with reverse temperature dependence of responsivity.

The radiation detector of the inventive optopaire comprises a Photodetector (PD) preferred embodiments of which comprise the band energy schematic structures set forth in FIG. 6 and FIGS. 17-18.

As was discussed herein above, like LEDs, photodetectors comprise two layers of semiconductor material. Each layer has a different type of conductivity, either n-type conductivity or p-type conductivity. Also like LEDs, they have a depletion region. Unlike LEDs however, when radiation in the form of photons hits the depletion area of the photodetectors, such photons generate electrons and holes. The motion of the generated electrons and holes in the depletion area creates a current whose signal can be measured precisely. But only when the ration of current signal to electron and hole generation noise is high.

To this end, i.e., to increase and improve the ration of signal to noise ratio by decreasing or suppressing electron and hole generation-recombination noise, the PD of the optopair of the present invention, optionally comprises the band energy schematic shown in FIG. 6. Its structure comprises n-type substrate, low n-type absorber, wide band gap barrier and p-type contact. The electrons and holes excited and generated or released in the low n-type absorber are separated at the absorber boundaries. The photo-generated holes cannot be transported into the n-type substrate because their access to it is blocked by the built-in electric field at the n-type substrate-absorber boundary. On the other hand, there is nothing blocking the movement of the photo-generated holes to the p-type contact. By comparison, direct transport of the photo-generated electrons to the p-contact is blocked by the wide band gap barrier. And since there is no electric field in the absorber, its thickness can be increased without corresponding increase in the electron holes generation-recombination noise.

In the preferred embodiment of the inventive optopair the PD comprises a sequence of a contact layer, a middle barrier layer and an n-type photon absorbing layer, said contact layer having a valence band, said n-type photon absorbing layer having a conduction band, said middle barrier layer having an energy bandgap significantly greater than that of the photon absorbing layer, and the top energy of said valence band of said contact layer is not more than the bottom energy of said conduction band of said n-type photon absorbing layer ("nBp photodetector"). Further, if the optopair of the present invention will be used for the detection and analysis of methane then the said n-type photon absorbing layer comprises Indium Arsenide.

In practice, one embodiment the nBp photodetector described above is an InAs-based nBp photodetector. It was grown on n-type ($1\times10^{18}$ cm$^{-3}$) InAs substrates using a Veeco GEN930 MBE system. The structure comprised undoped (weak n-type) 5 micron thick InAs absorber; 0.2 micron thick undoped AlAs$_{0.16}$Sb barrier and 0.4 micron thick p-type In$_{0.2}$GaAs$_{0.26}$Sb contact layer. The latter was. Be doped to $1\times10^{19}$ cm$^{-3}$. The composition of the contact layer was chosen to align the top of the valence band in the contact layer with the bottom of the conduction band of the absorber. Such alignment prevents charge transfer between contact and absorber and formation of build-in electric field since the latter can have negative effect on the detector's temperature performance.

Another embodiment of the nBp photodetector described above is a GaSb-based photodetector. It was grown on n-type (>5×10$^{17}$ cm$^{-3}$) GaSb substrates using a Veeco GEN930 MBE system. The structure comprised 0.5 micron thick n-type ($1\times10^{18}$ cm$^{-3}$) GaSb buffer layer, undoped (weak n-type) 3 micron thick In$_{0.36}$Ga$_{0.64}$As$_{0.32}$Sb absorber; 0.2 micron thick undoped Al$_{0.4}$GaAs$_{0.035}$Sb barrier and 0.3 micron thick p-type GaSb contact layer. The latter was Be doped to $1\times10^{19}$ cm$^{-3}$. The benefits of using this detector include complete transparency, thereby eliminating loss of photons, and control of the wavelength sensitivity of the detector through the manipulation of the composition of the absorber region of the detector.

Optionally, the optopair can comprise a bandpass filter matched to the absorption band of the gas of interest. If the optopair is to be used to detect and analyze methane, then the bandpass filter will be matched to the methane absorption band. The filter cuts off all the emission outside the methane absorption band which enhances relative magnitude of the absorbed emission. The filter is characterized by the spectral transmission function F(ω). For the ideal band pass filter transmitting in the spectral range from $\omega_1$ to $\omega_2$, $F(\omega)=\Theta(\omega-\omega_1)-\Theta(\omega-\omega_2)$, wherein $\Theta$ is the step function.

As was discussed above, the LED and the photodetector (PD) in the inventive optopair are chosen and arranged such that the at least one emission spectral maximum of the LED, and optionally, the responsivity spectral maximum of the PD, are de-tuned from the maximum absorption spectrum line of the absorption spectral band of the target gas analyte, such that the at least one emission spectral maximum of the LED and the responsivity spectral maximum of the PD are jointly or separately positioned on either the short side or the long side of the maximum absorption spectrum line of the absorption spectral band of the analyte gas. In one embodiment, for example, the at least one emission spectral maximum of the LED is de-tuned from, i.e., positioned on the short wavelength side of the maximum absorption spectrum line of the absorption band of the gas being analyzed, and the responsivity spectral maximum of the PD is de-tuned from, i.e., positioned on the long wavelength side of the maximum absorption spectrum line of the absorption band of the gas being analyzed with some overlap between the LED and PD Spectra within the absorption band of the gas being analyzed.

Figure 19:
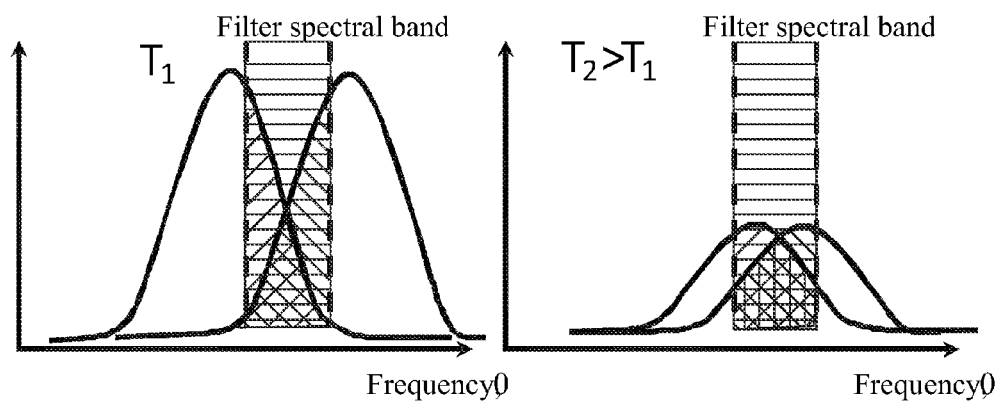
FIG. 19 is a schematic showing reciprocal compensation of LED and PD temperature dependencies.

This de-tuning of the LED spectrum, and optionally the PD spectrum as well, allows: a) for the compensation of the effect of temperature on their emission and responsivity spectra respectively, as the optical sensor is subjected to temperature variations, by permitting at least part of each of their emission and responsivity spectra to remain within the target analyte gas absorption band of interest, irrespective of the change of the intensity and shifting of their spectral maxima as a result of the effect of temperature (see FIGS. 7 and 19); and b) the optical sensor in which the inventive optopair is installed, to generate a signal that reliably, precisely and accurately provides for the identification and quantification of the target sample gas analyte irrespective of the temperature environment it is in.

The building of an optopair, capable of compensating for the effect of temperature on its signal, begins with the understanding that the temperature dependence of the optopair signal can be expressed mathematically by the following function:

$$S(T) \sim \int_{-\infty}^{\infty} E(T, \omega) R(T, \omega) F(\omega) d\omega, \quad (1)$$

where S(T) is the optopair signal, E(T, ω) is the normalized LED spectrum, R(T, ω) is normalized PD responsivity spectrum, and F(ω) is the spectral transmission function of the band pass filter.

Ideally, the optopair signal would not depend on temperature at all, i.e., S(T)=const(T). However, as was discussed above, the optopair signal does vary with temperature and the temperature sensitivity of the optopair can be characterized by the following parameter:

$$K \equiv \frac{S_{max}(T)}{S_{min}(T)} - 1 \quad (2)$$

where $S_{max}(T)$ and $S_{min}(T)$ are absolute maximum and minimum values of the expression (1) within the temperature range of the optopair operation.

Thus, it is clear from the foregoing that that one can build an optopair capable of minimizing the effect of temperature on its signal by compensating for the temperature sensitivities of the LED and the PD either separately or jointly. For example, in one of the optopair embodiments of the present invention, comprising a cascaded LED, the compensation for the temperature sensitivities of the LED and the PD occurs at the same time, by tailoring the E(T, ω), R(T, ω) and F(ω) in such a way that the temperature dependencies of the LED and PD spectra would compensate each other, such that the resulting temperature sensitivity of the optopair is low and the optical sensor consistently generates a signal sufficient to provide precise and accurate qualitative and quantitative analysis of a gas, irrespective of temperature.

On the basis of the foregoing then, the process of building an optopair capable of minimizing for the effect of temperature variation on its signal comprises the following steps: a) Identifying the target sample gas analyte; b) Establishing the frequencies/wavelengths that define the shortest, longest, and maximum spectral peak frequencies/wavelengths of the target sample gas analyte maximum absorbance spectrum ("the band pass filter"; also expressed as "the gas absorption band"); c) Using such frequencies/wavelengths to identify the material systems for the LED and the PD; d) Determining the spectral characteristics of the LED and PD materials and the temperature dependencies of said spectral characteristics. This can be done either experimentally by making and characterizing the test devices, or by referring to outside scientific references. Since semiconductor alloys are used to fabricate the LED and PD, the necessary information includes the dependence of the alloy band gap on its composition and temperature dependence of the luminescence amplitude and spectrum peak position of the alloys; e) Identifying the detuned target peak emission frequency and peak responsivity frequency of each of the LED and PD respectively through modeling of the LED emission and the PD responsivity spectra using the information generated by step (d); and f) finalizing the optopair design and fabricating the optopair. The goal of the process is the precise positioning of each of the optopair's LED spectral emission and PD spectral responsivity maxima, such that the temperature sensitivity of the optopair signal is minimized A. Identifying the Gas Absorption Band for the Sensor Operation.

The process of building an optopair capable of minimizing for the effect of temperature variation on its signal begins with the identification of the target gas sample analyte. For example the optopair can be built for the detection and analysis of methane. Or, it can be built for the analysis of Carbon Monoxide, or Carbon Dioxide, or Hydrogen Sulfide or Sulfur Dioxide, or any other gas present in the atmosphere. Once the target analyte gas is identified, such identification can then be used to determine the shortest, longest, and maximum absorption frequencies/wavelengths that define the target sample gas analyte absorption band. Such wavelengths can be found by referring to the target sample gas analyte maximum absorbance spectrum, which in turn can be found in any number of public sources including laboratory testing reference materials. The maximum absorbance spectrum will provide (i) the frequency and wavelength corresponding to the maximum absorption spectral line of the absorption spectral band of the target sample gas analyte, (ii) the frequency and wavelength corresponding to at least one spectral line on the short side of the maximum absorption spectral line, preferably the one that is the furthest away from and on the shortest side of the maximum absorption spectral line of the absorption spectral band of the target sample gas analyte, and (iii) the frequency and wavelength corresponding to at least one spectral line on the long side of the maximum absorption spectral line, preferably the one that is the furthest away from and on the longest side of the maximum absorption spectral line of the absorption spectral band of the target sample gas analyte. These frequecies and/or wavelengths can then be converted to energy units, i.e., electron volts, i.e., E(ev)=1.24/8(:), thereby establishing the range of energy which is further referred to as the gas analyte absorption band. For the successful operation of the optopair in the gas sensor, both LED emission and PD responsivity spectra have to overlap with this band. If the target gas sample analyte is methane, then the energy of the shortest, longest and maximum wavelengths of its IR absorption spectral band is 0.362 eV, 0.383 eV, and 0.367 eV respectively.

B. Determining the Material System for the LED and PD Structures.

Once the gas analyte absorption band is established, it is used to determine each of the material systems for the LED and the PD respectively. The material system for each of the LED and the PD respectively, is defined as the chemical composition of the LED or PD, respectively. The material system further refers to the material of the substrate, which determines the average lattice constant of the LED or PD structure, able to emit or absorb radiation having energy that coincides with the range of energy of the target gas analyte's absorption spectral band established above. Examples of LED and PD material systems capable of generating radiation within the absorption spectral band of methane include, but are not limited to, GaSb based material systems, or InAs based material systems, or TnP based material systems. One embodiment of a methane photodetector can comprise a InAs absorber whose band gap energy is fixed and coincides with the maximum absorbance spectrum peak of methane gas.

The choice of the material systems for the LED depends on whether the LED will be a bulk LED or a Quantum Well LED. And if it is a Quantum Well LED, whether it will have a single emission active area or whether it is a cascaded Quantum Well LED.

A bulk LED has an active area consisting of a single thick material capable of emitting radiation having a wavelength dependent strictly on the chemical composition of the material. By comparison, a Quantum Well LED has an active area consisting of one or more very thin layers of material capable of emitting radiation having a wavelength or energy dependent not only on the chemical composition of the material, but also on the layer width.

If the LED used in the optopair is a cascaded LED, then its spectrum is a superposition of several peaks centered at different frequencies. Each of the spectral peaks is produced by emission from one cascade or the group which includes several identical cascades. The number of the peaks corresponds to the number of the groups. The peak frequencies are determined by active area composition of each cascade while the relative intensities of the peaks are controlled by the number of the identical cascades in the group.

C. Determining the Spectral Characteristics of the LED and PD Materials and the Temperature Dependencies of Such Spectral Characteristics.

The establishing of each of the material systems for the LED and the PD respectively, is followed by the determination of the spectral characteristics of the chosen LED and PD materials. Such determination can be achieved experimentally, or can be achieved by referring to public sources and scientific literature. Spectral characteristics include but are not limited to, the respective dependence of the LED and PD alloy band gap on its composition and temperature dependence of the spectral shape, luminescence amplitude and spectrum peak position of the alloys.

The experimental determination of the spectral characteristics of the chosen LED or PD is suggested, if information is not publicly available, as in the case where a new material system is identified. Such determination includes fabrication of the LED or PD structure with their respective emission and responsivity spectral peaks close to the gas absorption band. The temperature dependencies of their respective emission and responsivity spectral shapes and positions can then be determined experimentally in the temperature range of interest.

D. Identifying the De-Tuned Target Peak Emission Frequency of Each of the LED and PD Respectively Through Modeling of the LED Emission and the PD Responsivity Spectra.

Once the determination of the spectral characteristics of the LED and PD materials and the temperature dependencies of said spectral characteristics is complete, it is used to identifying the target peak wavelength, de-tuned from the maximum spectral absorption peak wavelength of the target sample gas analyte for each of the LED and Photodetector emission and responsivity spectra respectively. Alternatively, the PD target peak wavelength can coincide with the maximum spectral absorption peak wavelength of the target sample gas analyte, instead of being detuned therefrom. The identification of the target peak wavelength is achieved through modeling of the LED emission and the Photodetector responsivity spectra using the information generated by the preceding steps and minimizing the temperature sensitivity of the optopair as determined by the technical requirements of the signal registration circuitry of the optopair.

As was discussed herein above, for all semiconductor alloys lattice matched to GaSb, the band gap energy, luminescence intensity and responsivity decrease with the increase of temperature. Thus, it follows that the electroluminescence intensity of semiconductor LEDs and responsivity of semiconductor PDs decreases with increase of temperature as well and that such decrease at higher temperatures can be compensated by increasing the LED emission spectrum or PD responsivity spectrum overlap with the gas analyte absorption band. Quantum Well LEDs have an advantage over bulk LEDs in connection with increasing the LED emission spectrum overlap with the gas analyte absorption band because Quantum Well LEDs provide for precise control of the LED spectrum position, not only by manipulating their chemical composition, but also by varying the widths of their optically active layers (quantum wells).

The overlap between the LED emission spectrum and/or the PD responsivity spectrum with the gas absorption band changes with temperature since, as the temperature changes, the spectra shift, while the gas absorption band does not. This effect can be fully or partially compensated by proper positioning of the LED and/or PD spectrum peaks with respect to the gas absorption band. For example, one can chose an LED and/or a PD with spectral maxima that are de-tuned to the high frequency side of the gas absorption band. As the temperature increases, the LED spectrum will shift to the lower frequency side of the gas absorption band. This will result in an LED spectrum which will overlap with the gas absorption band even moer, thus compensating for the drop in amplitude. This makes possible to maintain the overlap area of the LED spectrum and the gas absorption band within the limits which are necessary to provide a signal sufficient for the gas detection and quantification.

The mathematical modeling and the minimization of the temperature sensitivity of the optopair as determined by the technical requirements of the optopairs signal registration circuitry permits the achievement of the foregoing.

Based on the data obtained the determination of the spectral characteristics of the LED and PD materials and the temperature dependencies of said spectral characteristics, the LED emission spectrum $E(\omega,T)$ can be modeled at different temperatures. An example of the fitting function is given by the following expression:

$$E(\omega, \omega_{0E}, T) = e^{-\frac{T}{T_{E0}}} \sum_j E_j \exp\left[-\frac{(\bar{n}\omega - \bar{n}(\omega_{0E} - \omega_{Ej}) + \alpha_E T)^2}{2\Delta_{Ej}^2}\right] \quad (3)$$

Here $T_{E0}$, $\alpha_E$ and $\Delta_{Ej}$ are the material parameters determined in step (d); peak frequency $\omega_{0E}$ is determined by the active region composition, parameters $\omega_{Ej}$ and $E_j$ are chosen to best fit the spectrum shape of the LED emission, obtained during the determination of the spectral characteristics of the LED and PD materials and the temperature dependencies of said spectral characteristics. The fitting of the LED spectral shape is done at a fixed temperature, for example, room temperature. Parameters $T_{E0}$, and $\alpha_E$ allows obtaining LED spectrum at any temperature within the range of interest.

Once the LED Emission spectrum is modeled at different temperatures as discussed herein above, the information generated by such modeling is used to calculate the temperature dependence of the optopair signal and minimize the temperature sensitivity of the optopair in the temperature range of interest for use of the optopair. The Temperature dependence of the optopair signal can be characterized by the expression (1). For the ideal band pass filter transmitting in the spectral range from $\omega_1$ to $\omega_2$, $F(\omega)=\Theta(\omega-\omega_1)-\Theta(\omega-\omega_2)$, where $\Theta$ is the step function. So the expression (1) can be simplified as:

$$S(T) = \int_{\omega_1}^{\omega_2} E(T, \omega) R(T, \omega) d\omega \quad (4)$$

The minimization can be done numerically using the expression (2). An example of the minimization procedure which can be used is the nonlinear least square method. The result of this process is the magnitude WOE which determines the LED design. The target magnitude of Kmin is determined by technical requirements of the signal registration circuitry of the gas sensor. If Kmin can be reached using a single cascaded LED, then the optopair design can be finalized and the optopair can be fabricated.

Figure 16:
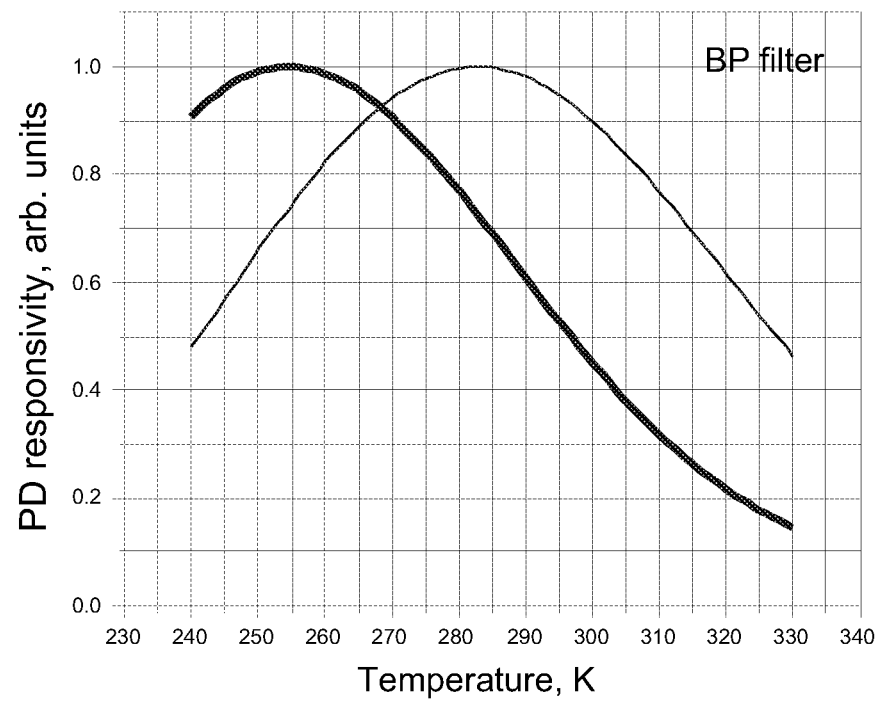
FIG. 16 is a schematic showing Temperature sensitivity of the optopair with maximized signal at room temperature (heavy black) and optopair with improved temperature stability (light black)

In case $K_{min}$ can not be reached using a one cascade LED, one can use LED with active area including several cascades. A multi cascade LED structure is two or more LED structures grown "in series'. Schematic layout of the two cascade LED structure is shown in FIG. 16. The LED spectrum is combination of two emission lines from the active regions. By changing the parameters of the active regions the position and shape of the resulting spectrum can be further controlled. The example is given in FIG. 17. Such control over the LED spectral shape gives another tool for compensation of the thermal drift of the optopair signal.

Application of a multi cascade LED gives additional minimization parameters so the compensation of the temperature dependence of the optopair signal can be done more accurately. Now, general expression for the fitting function is:

$$E(\omega, \omega_{0E1}, \omega_{0E2} \ldots \omega_{0En}T) = \Sigma_n N_n E(\omega - \omega_{0En}) \quad (5).$$

Here $N_n$ is the number of identical LED cascades emitting at frequencies $\omega_{0En}$. The procedure of minimization should be repeated iteratively until the required $K_{min}$ is reached. The number of cascades is increased by one at each iteration. The result of the procedure is the set of the parameters $N_n$, and $\omega_{0En}$ which determine the LED design.

Figure 13:
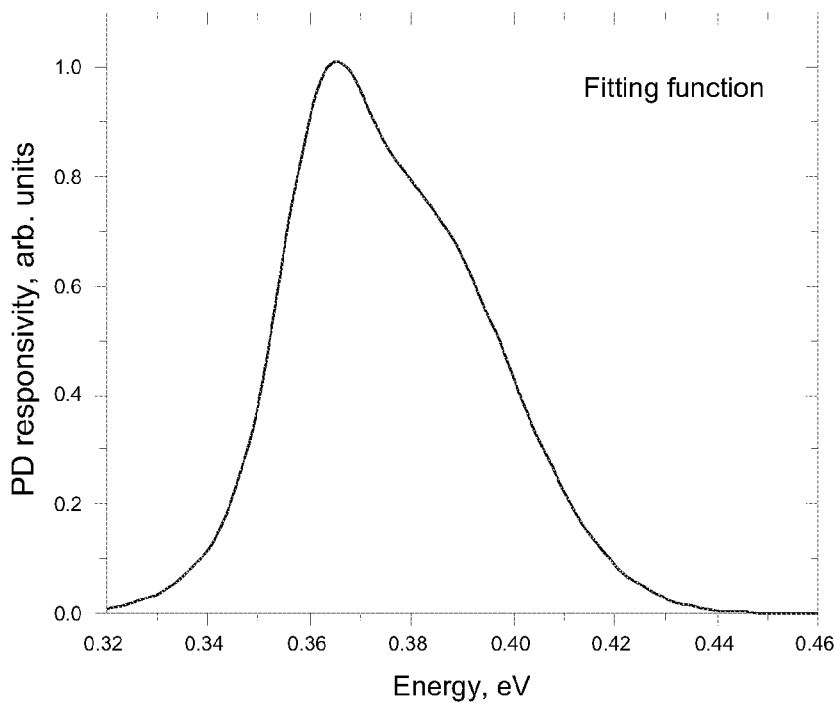

The PD responsivity spectrum is determined by the absorber band gap as well. To this end, quaternary alloy InGaAsSb can be used as the PD absorber material. Variation of the alloy content is a way to control the alloy's band gap energy while maintaining same lattice constant. The latter is a necessary condition for high quality PD fabrication. A band diagram of one of the proposed photo detectors is shown in FIG. 13. The advantages of the proposed structure are the possibility of the band gap control through the absorber alloy composition and the transparency of the substrate in the spectral range of sensitivity (backside illumination possible).

The information on the PD spectrum and its temperature dependence gathered in step (d) herein above, can then be used to model the PD responsivity spectrum at different temperatures, using the fitting function given by the following expression:

$$R(\omega, \omega_{0E}, T) = e^{-\frac{T}{T_{R0}}} \sum_i E_i \exp\left[-\frac{(\hbar\omega - \hbar(\omega_{0R} - \omega_{Ri}) + \alpha_R T)^2}{2\Delta_{Ri}^2}\right]. \quad (6)$$

Here $T_{R0}$, $\alpha_R$ and $\Delta_{Ri}$ are the material parameters determined in step (d); peak frequency $\omega_{0R}$ is determined by the PD absorber composition, parameters $\omega_{Ri}$ and $R_i$ are chosen to best fit the spectrum shape of the PD responsivity, obtained in step (d). The fitting of the PD spectral shape is done at a fixed temperature, for example, room temperature. Parameters $T_{R0}$, and $\alpha_R$ allows obtaining PD responsivity spectrum at any temperature within the range of interest.

Once the PD responsivity spectrum is modeled at different temperatures, the information generated by such modeling is used to calculate the temperature dependence of the optopair signal and minimize the temperature sensitivity of the optopair using the procedure discussed herein above in connection with the LED minimization. The result of this process is the magnitude $\omega_{0R}$ which determines the PD design.

Figure 7:
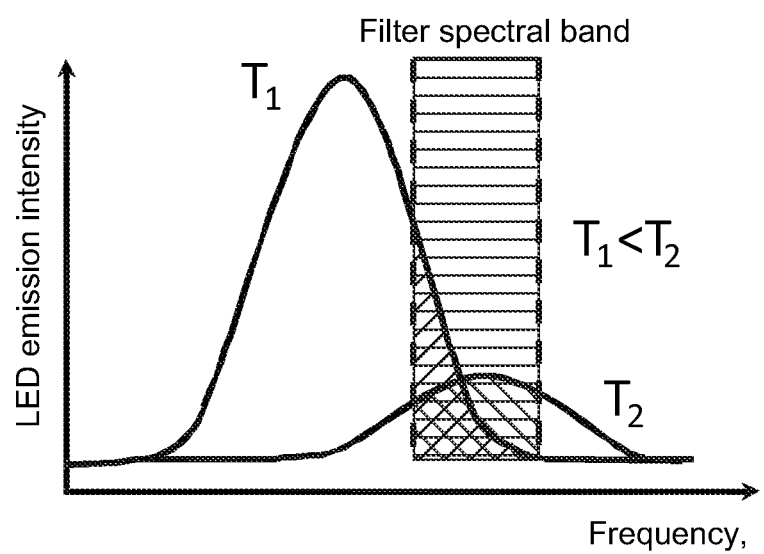
FIG. 7 is a schematic LED spectrum whose spectral maximum is de-tuned from the maximum absorption spectrum line of the absorption spectral band of the target gas analyte, at two temperatures and the portion of such LED spectrum area remaining within such absorption spectral band. The LED spectral portion within the filter band remains relatively constant.
Figure 8:
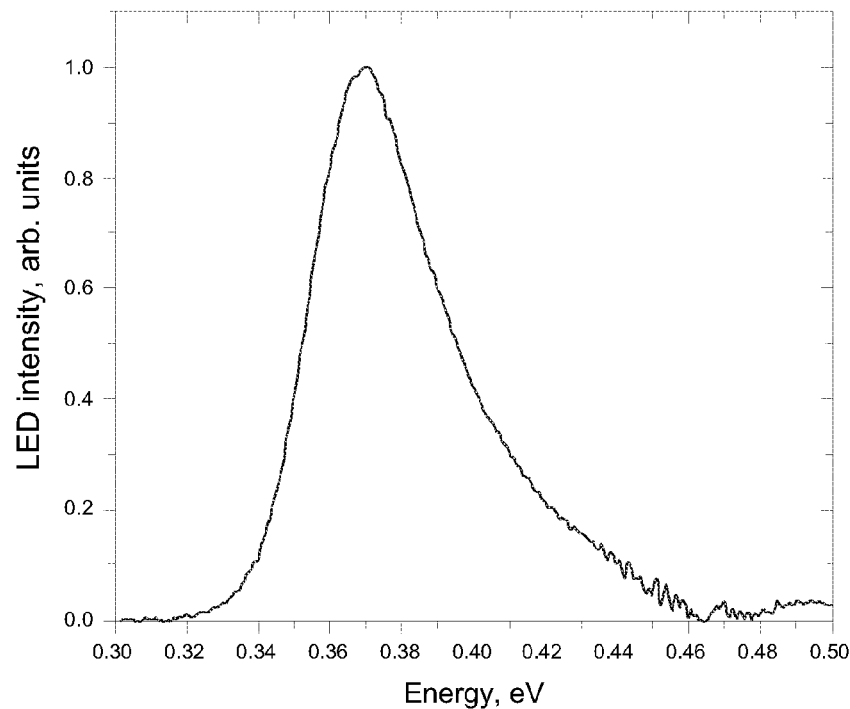
FIG. 8 is an experimental long wavelength edge of an LED spectrum at a specific temperature.
Figure 9:
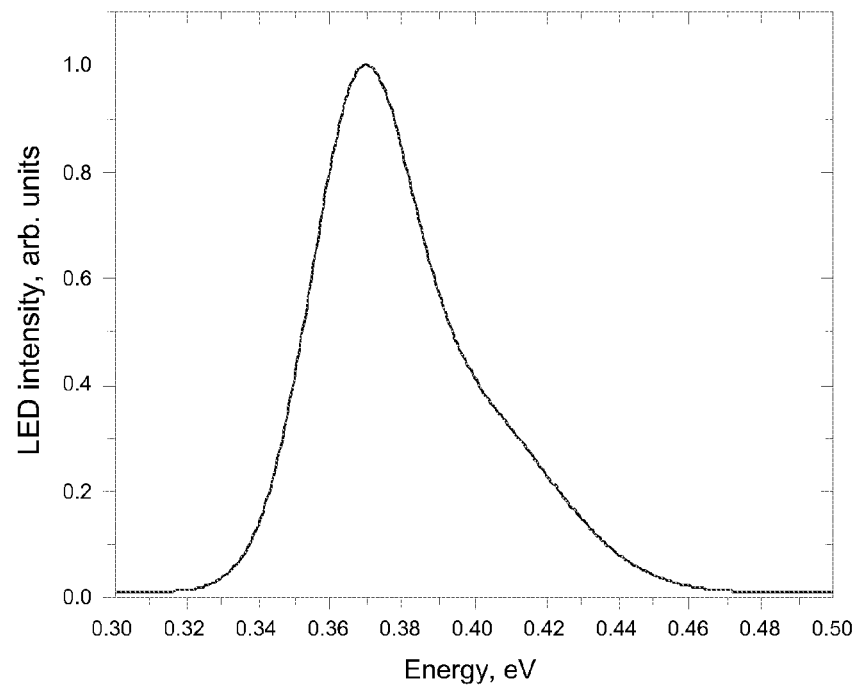
FIG. 9 is a schematic Gaussian fit of the long wavelength edge of the LED spectrum of FIG. 8 herein above.
Figure 10:
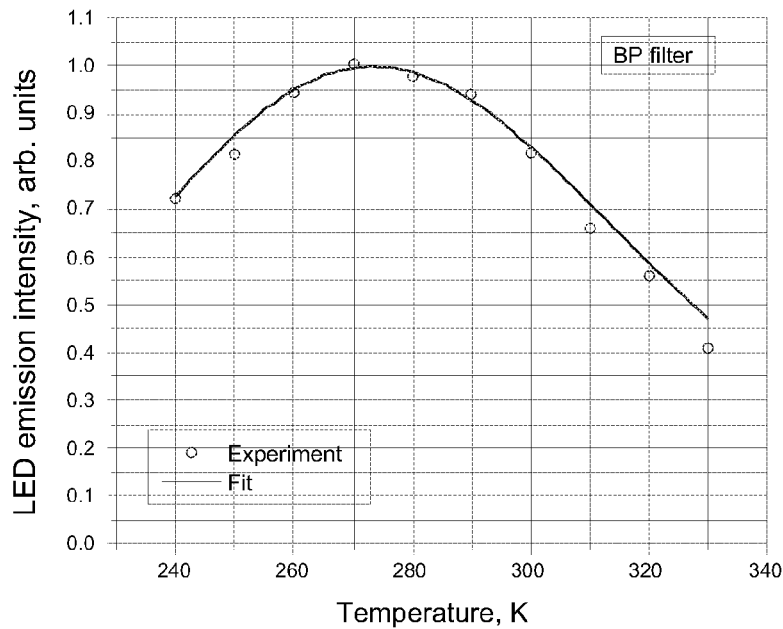
FIG. 10 shows experimental data obtained on LED with spectrum peak at 0.367 eV (hollow circles) corresponding to LED spectrum generated via mathematical modeling.
Figure 11:
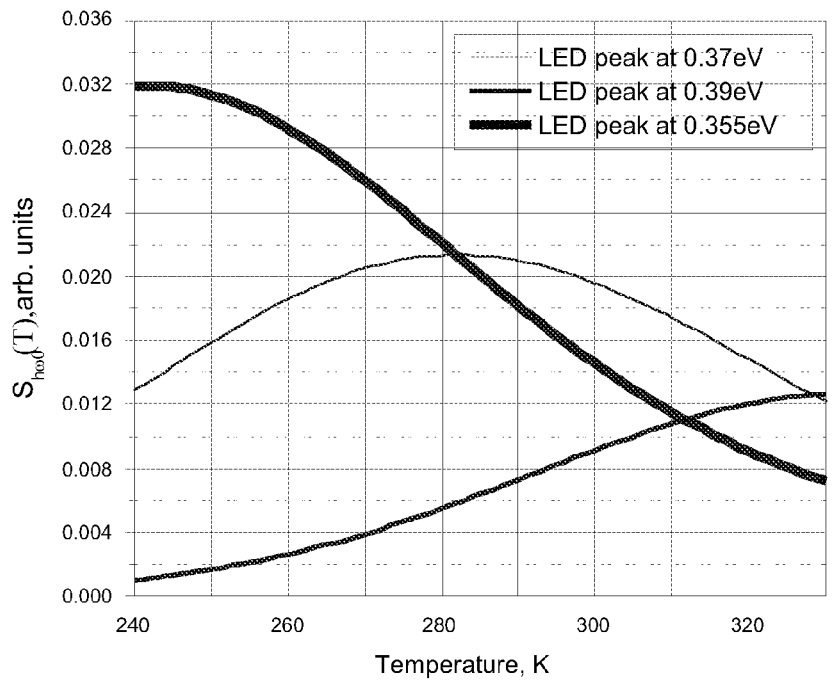
FIG. 11 is $S_{\hbar\omega 0}(T)$ at different positions of the LED spectrum peak.
Figure 12:
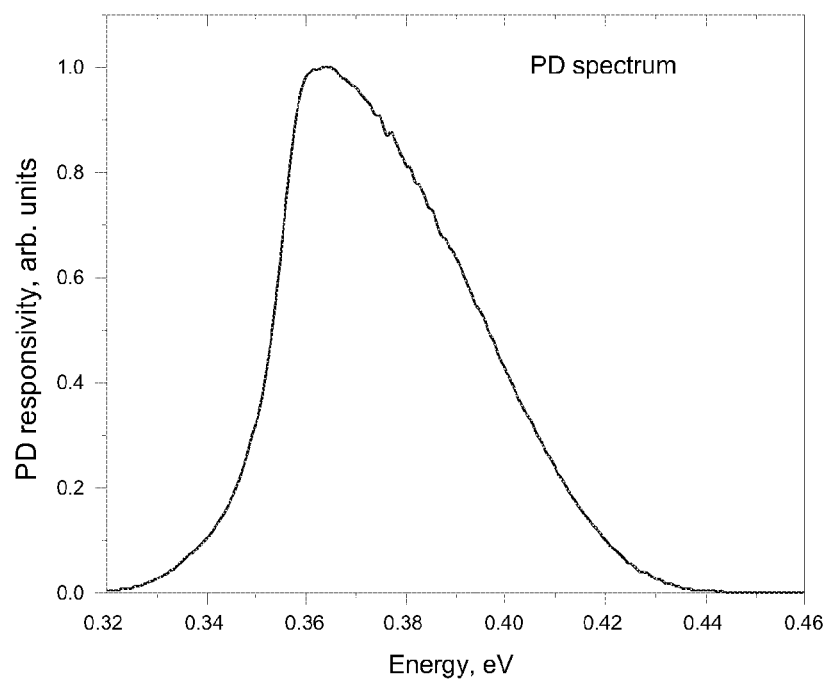
FIGS. 12 and 13 show experimental and modeled responsivity spectrum and of the optopair photodetector respectively.
Figure 14:
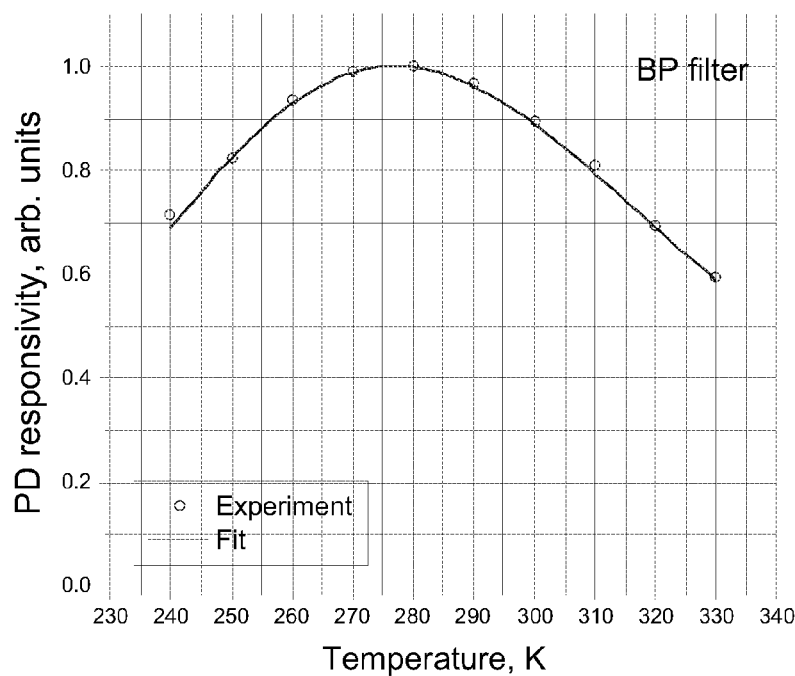
FIG. 14 is a schematic showing PD integral responsivity with the filter pass band; experiment (hollow circles) and fit (line)

One way is to make the PD more responsive at high temperatures. To that end an additional potential barrier for the photo exited holes can be 19 added (FIG. 7). There are two ways for the holes, photo exited in the absorber. One way is to tunnel through the barrier and get captured in the p-contact. The other way is to recombine back with an electron in the absorber. The latter way does not make any contribution to photocurrent. Both ways are shown as dash green arrows in FIG. 14. The probability ratio of these two ways is determined by temperature and the barrier height DE. As a characteristic thermal energy kT (k is the Boltzmann constant) is much less than DE, the photo exited carrier with high probability will recombine in the absorber and photocurrent will be low. At higher temperature, as kT becomes comparable with DE, the photo exited carriers can penetrate to the p-contact and photo current is increasing. Responsivity of the detector will be higher at higher temperatures. This temperature dependence will fully or partially compensates the decrease of the LED intensity at high temperatures. The strength of the temperature dependence of the PD can be controlled through the bather height.

Figure 15:
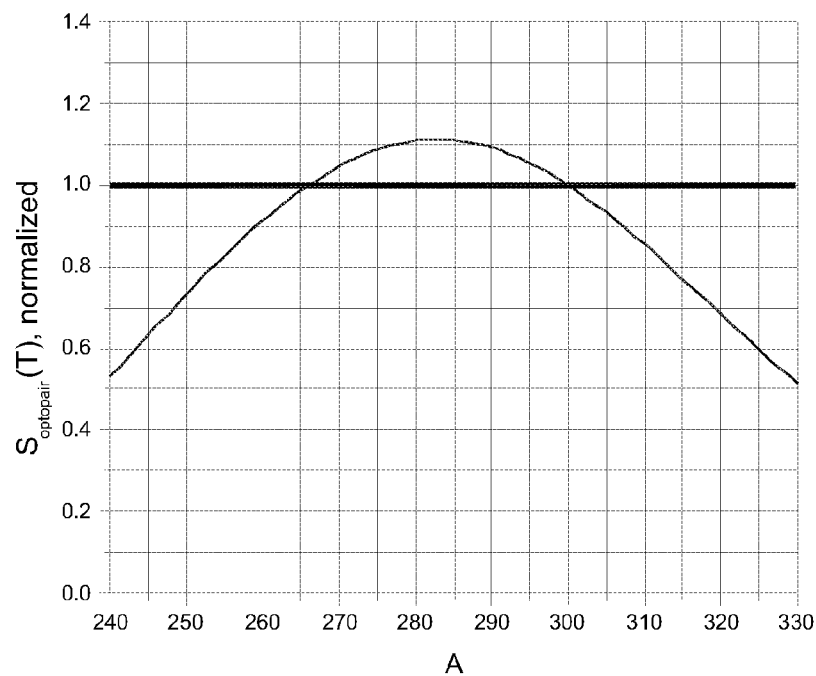
FIG. 15 is a schematic showing simulated temperature sensitivity of the opto pair corresponding to the LED emission peak at 0.37 ev.

Another way to compensate for the temperature dependence of LED intensity is the application of mercury-cadmium-telluride (MCT) photo detectors. The bandgap energy of MCT materials increases with temperature. This is opposite to corresponding dependence in GaSb-based materials. The responsivity amplitude of MCT detectors is decreasing with temperature. At low temperature, the LED emission spectrum and PD responsivity spectrum can be shifted to shorter- and longer wavelength sides of the filter band (FIG. 15).

It is a clear from the foregoing that the optical gas sensor, which incorporates the inventive optopair described above will be portable, light to carry, relatively inexpensive to manufacture and produce, capable of consuming very little power and equipped to deliver accurate and reliable qualitative and quantitative analysis of gases at multiple temperatures and at low concentrations. It will accurately and precisely detect and measure the concentration of a gas, irrespective of temperature, as a result of the optopair's structure and its ability to compensate for temperature susceptibility of the optopair signal. As a result, it will reliably and effectively detect and measure the absorbance of gas in environments across a broad range of temperatures, at low concentrations. More particularly, an optical gas sensor incorporating an optopair designed and fabricated in accordance with the foregoing for the detection and analysis of methane, will not only be capable of identifying and measuring the absorbance of methane, but will be able to do so at below the lower explosive limit (LEL) of methane, i.e., 5% by volume in atmosphere. A solution to a problem that is long overdue.

While particular embodiments of the invention have been illustrated and described in detail herein, they are provided by way of illustration only and should not be construed to limit the invention. Since certain changes may be made without departing from the scope of the present invention, it is intended that all matter contained in the above description, or shown in the accompanying drawings be interpreted as illustrative and not in a literal sense. Practitioners of the art will realize that the sequence of steps and the embodiments depicted in the figures can be altered without departing from the scope of the present invention and that the illustrations contained herein are singular examples of a multitude of possible depictions of the present invention.

Accordingly, and based on the materials described above we claim:

1. A process or building an LED and Photodetector optopair for use in optical sensors for analysis of a target sample gas analyte, said optopair being able to compensate for the effect of temperature variation on its signal comprising the following steps:
- a. identifying the target sample gas analyte;
- b. establishing the target sample gas analyte absorption band by determining its shortest, longest, and maximum spectral peak wavelengths;
- c. using said shortest, longest and maximum spectral peak wavelengths to determine the material systems for each of the LED and the Photodetector respectively;
- d. determining the spectral characteristics of the LED and Photodetector materials and the temperature dependencies of said spectral characteristics;
- e. identifying the target peak wavelength for each of the LED and Photodetector emission and responsivity spectra respectively through modeling of the LED emission and the Photodetector responsivity spectra using the information generated by the preceding steps and minimizing the temperature sensitivity of the optopair as determined by the technical requirements of the signal registration circuitry of the optopair, such that each of the target peak wavelengths of the LED and Photodetector emission and responsivity spectra respectively is detuned from the maximum spectral absorption peak wavelength of the target sample gas analyte, a portion said LED emission spectrum overlaps a portion of said Photodetector responsivity spectrum, said overlapping spectral portions remaining within said target sample gas analyte absorption band, and the area of said overlapping spectral portions within said target sample gas analyte absorption band remaining constant notwithstanding temperature variations; and
- f. finalizing the optopair design and fabricating same.

2. The process of building the LED and Photodetector optopair of claim 1 wherein the step of minimizing the temperature sensitivity of the optopair as determined by the technical requirements of the signal registration circuitry of the optopair further optionally comprises the step of identifying the target peak wavelengths for a multi-cascade LED emission spectrum.

* * * * *